(12) United States Patent
Dalloro et al.

(10) Patent No.: US 8,247,622 B2
(45) Date of Patent: Aug. 21, 2012

(54) PROCESS FOR THE PREPARATION OF PHENOL

(75) Inventors: Leonardo Dalloro, Bollate-Milano (IT); Alberto Cesana, Galliate-Novara (IT); Roberto Buzzoni, San Mauro Torinese (IT); Fausto Genoni, Milan (IT); Guido Spano, Novara (IT); Franco Rivetti, Milan (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 12/908,583

(22) Filed: Oct. 20, 2010

(65) Prior Publication Data

US 2011/0092746 A1 Apr. 21, 2011

Related U.S. Application Data

(62) Division of application No. 11/813,874, filed as application No. PCT/EP2006/000160 on Jan. 10, 2006, now Pat. No. 7,868,210.

(30) Foreign Application Priority Data

Jan. 20, 2005 (IT) ............................... MI2005A0062

(51) Int. Cl.
*C07C 37/00* (2006.01)
(52) U.S. Cl. ........................................ 568/800; 568/802
(58) Field of Classification Search .................. None
See application file for complete search history.

(56) References Cited

U.S. PATENT DOCUMENTS 5,756,861 A * 5/1998 Panov et al. .................. 568/800
2001/0044559 A1 * 11/2001 Hamilton, Jr. ................ 568/803

FOREIGN PATENT DOCUMENTS

| DE | 501 467 | 7/1930 |
| DE | 849 557 | 9/1952 |
| EP | 1 411 038 | 4/2004 |
| GB | 2 066 815 | 7/1981 |
| JP | 48 061439 | 8/1973 |

OTHER PUBLICATIONS

Emig et al., Topics in Catalysis vol. 21., No. 1 (2002).*
Jelinek, et al., "Partial dehydroxylation of pyrocatechol and mixtures of dihydric phenols under pressure", Chemicky Prumysl, XP002271913, 1956. (Abstract only).
Matthias, "Konventionelle und Kombinatorische Suche nach neuen Katalysatoren fuer die selektrive Oxidation von Benzol zu Phenol", Einleitung und Problemstellung, pp. 1-140, XP002343627, 2000.
Yamanaka, et al., "Direct Synthesis of Phenol from Benzene with $O_2$ over Vmo-Oxide/$SiO_2$ Catalyst", Studies in Surface Science and Catalysis, vol. 130, pp. 809-814, XP008052138, 2000.
Emig, et al., "New reaction engineering concepts for selective oxidation reactions", Topics in Catalysis, vol. 21, No. 1-3, pp. 11-24,618 XP002343628, 2002.

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

A process is described for the preparation of phenol by the hydrodeoxygenation of polyhydroxylated benzene derivatives or by the selective hydroxylation of benzene under depletive conditions, characterized in that the above-mentioned reactions are carried out in the presence of a catalyst based on multi component metal oxides comprising at least one metal selected from the groups VB, VIB, VIII, IB, IIB, IVA, VA.

18 Claims, 4 Drawing Sheets

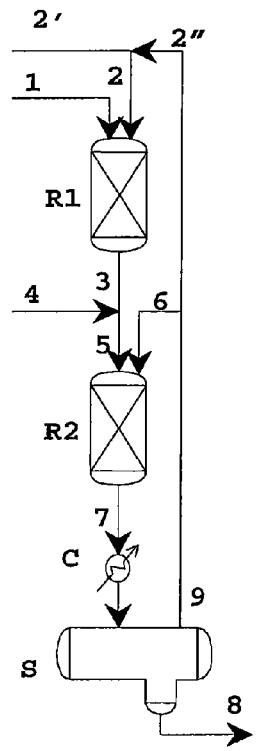

R1. First reactor
R2. Second reactor
C. Condenser
S. Gas-liquid separator
1. Benzene-diols in aqueous solution, feeding R1
2. Hydrogen feeding R1
2'. Fresh hydrogen, feeding R1
2". Recycled hydrogen, feeding R1
3. Outgoing stream from R1
4. Cooling water
5. Cooled mixture, feeding R2
6. Recycled hydrogen, feeding R2
7. Outgoing stream from R2
8. Aqueous solution of raw phenol
9. Hydrogen for recycling Figure 1. Scheme of the equipment for the hydrodeoxygenation of benzene-diols in two steps.

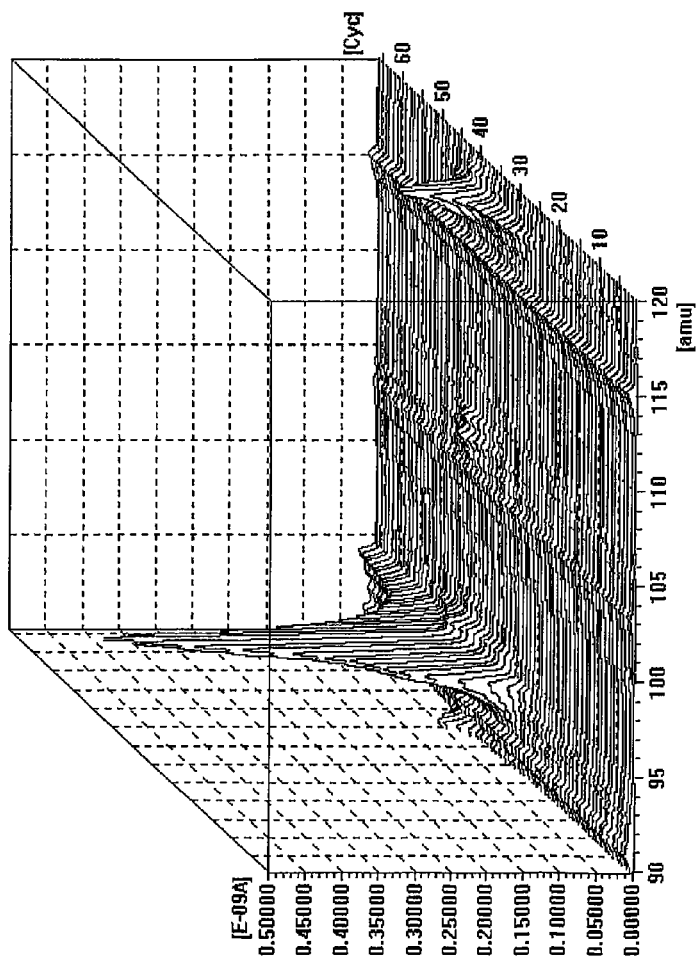
Figure 2. Trend of the masses from AMU 90 to AMU 120 in relation to the measurement cycle of the experiment carried out in Example 17. AMU 94 = Phenol, AMU 118 = benzofuran. The peaks which keep the I.C. unvaried are impurities due to the feeding.

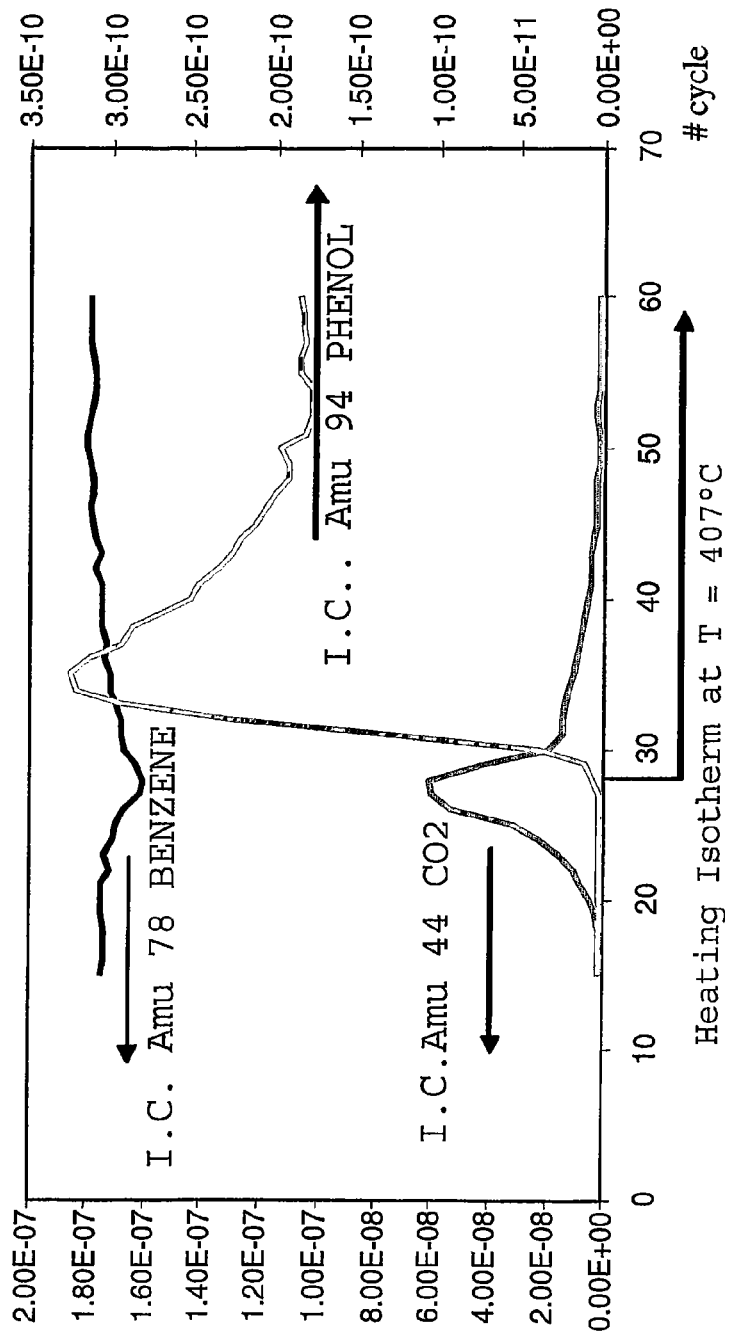
Figure 3. Trend of the masses corresponding to phenol (AMU 94), $CO_2$ (AMU 44) and benzene (AMU 78) during the heating and isotherm at 407°C of the experiment carried out in Example 18

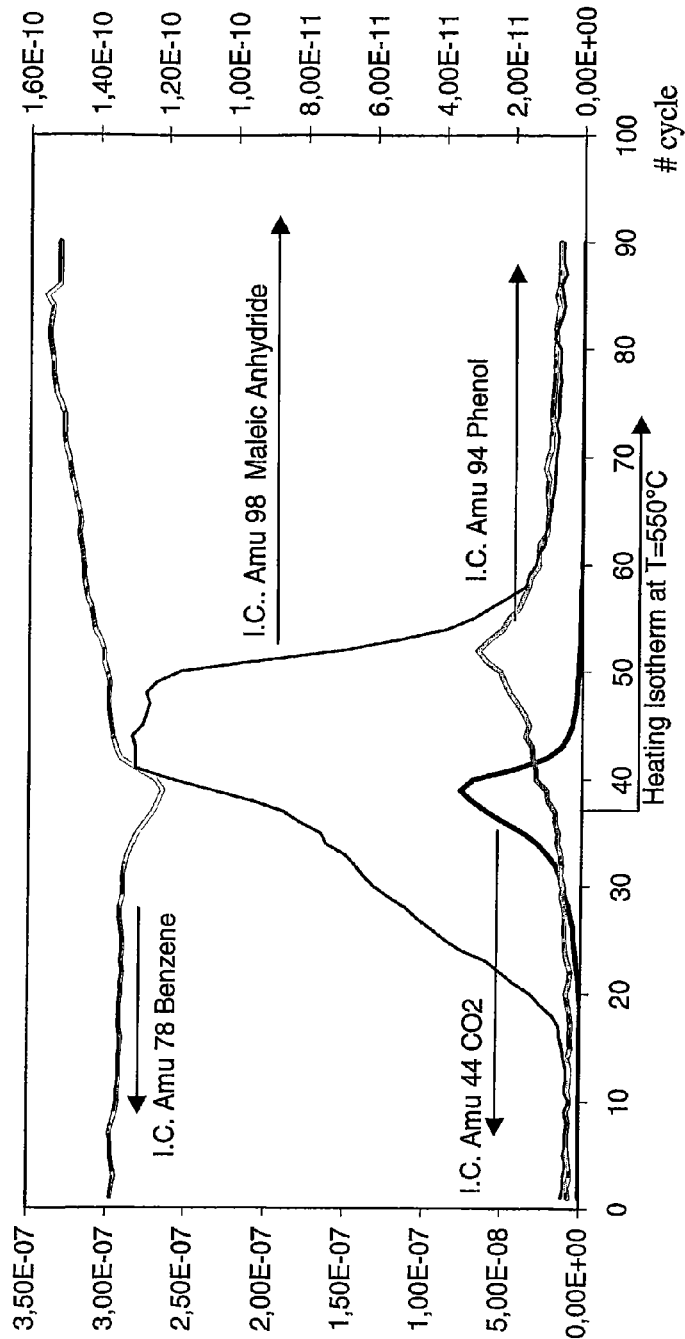
Figure 4. Trend of the masses corresponding to maleic anhydride (AMU 98), phenol (AMU 94) CO2 (AMU 44) and benzene (AMU 78) during the heating and isotherm at 550°C of the experiment carried out in Example 19.

PROCESS FOR THE PREPARATION OF PHENOL

The invention relates to a process for the preparation of phenol by the hydrodeoxygenation of benzene-diols with hydrogen or through the direct oxygenation of benzene.

More specifically, it relates to a process for the preparation of phenol wherein the above-mentioned reactions are carried out in the presence of a catalyst based on multi-component metal oxides.

Phenol is an intermediate product of great importance which is applied in several industrial sectors such as, for example, in the production of polycarbonates or other phenolic resins, in fibres, detergents, antioxidants and numerous other fields.

Phenol is produced on an industrial scale starting from cumene, through a multi-step process which starts from benzene and propylene and leads to the co-formation of phenol and acetone. The co-production of acetone may cause disposal problems in the future, as a slower market growth is expected of this product with respect to that of phenol.

Research is therefore being actively carried out for an alternative commercial process, with the aim of simplifying the existing process.

The research lines currently followed propose processes both in liquid and gas phase.

In U.S. Pat. Nos. 6,573,413 and 5,110,995, for example, a "one-step" process is described, in gas phase, starting directly from benzene and nitrous oxide (Alphox process). One of the major problems of this process is linked to the availability of the oxidant. The production ad hoc of nitrous acid ($N_2O$) as oxidant, starting from ammonia, is, in fact, onerous, whereas the possibility of using $N_2O$ as by-product of the production of adipic acid from phenol, seems to be an important factor for the economical feasibility of the Alphox process. This, however, requires a strong integration between the two processes, which is unfavourable for the running of independent dynamics in the product market.

The study of alternative processes for the preparation of phenol based on the direct oxidation of benzene, at a high temperature, in gas phase, through molecular oxygen or air, in the presence of various oxidation catalysts, has so far not given acceptable results either with respect to the intrinsic safety of the process or to performances.

Unfortunately, at the temperatures used in these processes, also large oxidations of the benzene ring take place, which lead to the formation of products such as carbon dioxide, carboxylic acids or anhydrides, with a consequent loss of selectivity (U.S. Pat. No. 5,981,424; G.I. Panov CATTECH 4 (2000), 18-32; J. Plotkin, European Chemical News 25 Sep.-1 Oct. 2000, 59-62).

Another drawback of direct oxidation in gas phase, wherein oxidants (for example oxygen) and hydrocarbons are co-fed, is represented by the possibility of falling within the flammability limits or explosiveness of the reagent mix; these limits are often only known in an approximate way, under the temperature conditions, pressure, geometry characteristics of industrial plants (P. Arpentier F. Cavani, F. Trifirò, The technology of catalytic oxidation, vol 2 Safety aspects, Ed. Technip, 2001).

Patents EP 0919531 and EP 0958861, describe the selective oxidation of benzene, without causing the breakage of the benzene ring, operating in liquid phase and using oxidants such as hydrogen peroxide, in the presence of specific solvents and suitable catalytic systems. These processes, however, do not allow high productivity levels to be reached as they must be run at low conversions of benzene in order to limit the consecutive oxidation reactions of phenol to by-products (catechol and hydroquinone).

Patent application WO 03042146, for example, specifies that 111 kg of hydroquinone and catechol (in a 55/45 mix) are co-produced for each ton of phenol, with a benzene conversion of 12.2% and a selectivity to phenol of 90%. These by-products are in such a quantity that they cannot be absorbed by the market and must therefore be disposed of introducing additional costs to the process.

Another preparation method of phenol envisages starting from benzene-diols, subjecting these compounds to a hydrodeoxygenation process with hydrogen, operating in the presence of water and with a catalyst based on elements of group VIB or VIII of the periodic table, as described in European patent application EP 1411038.

The integrated process for the preparation of phenol described in Italian patent application EP 1424320A1 wherein the reaction by-products hydroquinone and catechol are selectively transformed into phenol and recycled in the process flow streams, allows the co-production of byproducts to be completely eliminated, obtaining an increase in the productivity to phenol.

It has now been found that phenol can be prepared starting from both polyhydroxylated benzene derivatives (for example benzene-diols), through hydrodeoxygenation in the presence of hydrogen, and also from benzene through oxidative hydroxylation (also defined as direct partial oxidation) carried out in a depletive environment, operating in the presence of particular catalytic compositions.

BRIEF DESCRIPTION OF THE DRAWINGS

FIG. 1 shows a schematic of equipment suitable for carrying out an embodiment of the process of the invention;

FIG. 2 shows the trend of atomic mass unit in relation to the measurement cycle in an experiment of one embodiment of the invention;

FIG. 3 shows trends of mass values of benzene, phenol and carbon dioxide during heating in one aspect of the invention; and FIG. 4 shows trends of maleic anhydride, phenol, carbon dioxide and benzene during heating at 550° C. in one embodiment of the invention.

A reaction carried out in a depletive environment means a reaction effected with a deficit of molecular oxygen or other oxidizing agents with respect to the stoichiometry of the reactions.

This condition is reached by feeding oxygen to the reaction or other oxidizing agents in lower or null amounts with respect to the stoichiometric quantity due to the converted benzene, as better illustrated hereunder.

An object of the present invention therefore relates to a process for the preparation of phenol through the hydrodeoxygenation of polyhydroxylated benzene derivatives or through the selective hydroxylation of benzene under depletive conditions, characterized in that said reactions are carried out in the presence of a catalyst based on multi-component metal oxides, comprising at least one metal selected form groups VB, VIB, VIII, IB, IIB, IVA, VA.

The capacity of the catalysts of the invention of being used in the depletive oxidative hydroxylation of benzene or in the hydrodeoxygenation of polyhydroxylated benzene derivatives in the presence of hydrogen is even more surprising when considering that the typical oxidation and reduction catalysts are not capable of effecting the reactions described, as demonstrated by the comparative examples indicated.

In the case of depletive oxidative hydroxylation, the complementary stoichiometric oxygen is provided by the catalyst, which, at the same time, modifies its composition (conversion phase of benzene to phenol and reduction phase of the catalyst). In a subsequent phase, the catalyst is restored to its original state by means of oxygen or another oxidizing compound (re-oxidation phase of the catalyst). The reaction and re-oxidation phases are effected cyclically.

In the oxidation step of benzene to phenol, the catalyst is used in partial or total oxidised form, and maintained with a deficit of oxygen, or other oxidising agent, under the reaction conditions.

In practice, the oxidation reaction of benzene to phenol is carried out in the absence of molecular oxygen or other oxidising agents, or by feeding lower amounts of oxygen, or other oxidising agents, than the quantity required by the stoichiometry of the converted benzene.

From reaction (1), illustrated below, it is evident that the catalyst participates in the stoichiometry of the reaction also acting as reagent, when it is in an oxidative state (catox), capable of providing part of its oxygen and subsequently assuming a reduced state (catred).

In order to make the reaction catalytic, it is necessary for the reduced catalyst to be capable of easily recovering the oxygen from an oxidative agent (for example air, oxygen, $N_2O$, etc.) to be re-transformed, in a second step (2), into a higher oxidation state, useful for initiating a new oxidative cycle.

The oxidation state of the catalyst in its oxidised form can be the maximum oxidation state or an intermediate oxidation state, optimal for maximising the desired reaction parameters (yields, productivity, etc.).

$$C_6H_6 + catox \rightarrow C_6H_5OH + catred \quad (1)$$

$$catred + ox \rightarrow catox \quad (2)$$

wherein ox is one of the above-mentioned oxidising agents.

Within the range of selective catalytic oxidation reactions, the depletive approach (hereinafter called "RedOx technology") is known (Ind. Eng. Chem., 41(6), 1949, page 1227).

This approach was developed both for selective oxidation reactions and for oxidative dehydrogenation.

In particular, the RedOx technology for selective oxidation reactions, as introduced in the present patent, can be traced back to engineering concepts which contemplate functioning with periodical operations. The latest developments of these technologies are described by G. Emig and M. A. Liauw in Topics in Catalysis Vol. 21, Nos. 1-3 (2002) page 11-24 and by P. Silveston, R. R. Hudgins, A. Renken in Catalysis Today 25 (1995) 91-112.

The oxidation process of benzene using the RedOx technology is carried out in a reactor operating at temperatures ranging from 150 to 700° C., preferably from 200 to 600° C. and even more preferably from 250 to 550° C., at a pressure ranging from 0.1 to 100 bar, preferably from 1 to 30 bar, with space velocities, in terms of Weight Hourly Space Velocity WHSV (grams of feeding mix per gram of catalyst per hour) ranging from 0.01 to 1000 $h^{-1}$ preferably from 1 to 100 $h^{-1}$ and even more preferably from 2 to 50 $h^{-1}$.

The reaction can be effected in the presence of a diluent ($N_2$, $CH_4$, $H_2O$, $CO_2$, etc.) The catalytic system is restored in a regenerator, at temperatures higher than 100° C., thus re-establishing an oxidative state more useful for the catalyst and possibly eliminating at least part of the carbonaceous pitches deposited during the reaction.

The oxidising environment used in this section can consist of oxygen, air, suitable nitrogen-oxygen mixtures, other oxidising agents such as, for example, $N_2O$ and blends thereof. The presence of diluents such as $CO_2$, $H_2O$, etc. is also possible.

The oxidation reaction of the organic substrate is preferably effected outside the explosion ranges of the gaseous reagent mix for the temperature, pressure and oxygen/air ranges used.

The hydroxylation reaction of benzene of the invention is preferably carried out in two reactors: one destined for the reaction, the other for regeneration.

In this way, it is possible to separate the hydrocarbon from the oxidising agent, thus obtaining various advantages with respect to oxidation in gas phase wherein the substrate and the oxidising agent are contemporaneously fed.

In particular, the separation of the organic and oxidation streams in the reactor allows:

the use of air as oxidising agent instead of oxygen, without the nitrogen interfering in the product separation a greater selectivity, as there is no direct interaction between the organic substrate fed and the molecular oxygen the possibility of feeding more concentrated streams without the risk of explosions, due to the separation between air/oxidising gas and hydrocarbons.

the formation of a more concentrated product at the reactor outlet optimisation of the yields through a suitable regulation of the reaction conditions (composition and feeding flowrate, catalyst re-oxidation frequencies, oxidation state of the catalyst at the beginning and at the end of the reaction phase).

The selective hydroxylation process of benzene is normally effected in several reactors, at least one of which is dedicated to the regeneration of the catalyst; in this case at least one reactor is destined for the regeneration of the catalyst which is effected either by means of a physical moving of the catalyst from the reaction reactor to the regeneration reactor, or by means of an exchange of flows between them.

When fluid bed reactors are used, the reaction and regeneration phases can also be effected inside the same equipment, according to the state of the art.

Fluid bed reactors of the fast fluid bed, or riser-downcomer type can be advantageously used for carrying out the hydroxylation at low contact times.

If the phenol is obtained by the hydrodeoxygenation of polyhydroxylated benzene derivatives, for example benzenediols, the process is effected by reacting the polyhydroxylated benzene derivatives with hydrogen in vapour phase at a temperature of 250-500° C., preferably 300-450° C., at a pressure of 1-100 bar, preferably within the range of 3-50 bar, and at a space velocity (WHSV=Weight Hourly Space Velocity, as kg of benzenediols/h/kg of catalyst) of 0.1-10 $h^{-1}$, preferably 0.5-5 $h^{-1}$.

Water is a convenient reaction medium for this reaction, it is, in fact, an optimum solvent for the reagents and reaction products and is also completely inert towards both of them.

Water also has the advantage of having a high thermal capacity and therefore has the property of restraining the temperature increase due to the enthalpy of the deoxygenation reaction. Finally, water is also particularly economical.

In the process through the hydrodeoxygenation of benzene-diols, it is possible to convert to phenol, with a high efficiency and selectivity, 1,2-benzenediol (catechol, hereinafter in short 1,2-BD), 1,3-benzenediol (resorcinol, hereinafter 1,3-BD), 1,4-benzenediol (hydroquinone, hereinafter 1,4-BD) and blends thereof.

The reaction is carried out in vapour phase at a temperature of 250-500° C., preferably 300-450° C., at a pressure of 1-100 bar, preferably within the range of 3-50 bar and at a space velocity (WHSV=Weight Hourly Space Velocity, as kg of benzene-diols/h/kg of catalyst) of 0.1-10 $h^{-1}$, preferably 0.5-5 $h^{-1}$.

The reactor feed stock consists of a solution of benzene-diols in water at a concentration of 5-60% by weight, preferably 10-40% by weight, and hydrogen with a molar ratio with respect to the benzene-diols of 2-50, preferably 5-30.

In an embodiment of the invention, the reaction is carried out inside an adiabatic, fixed bed reactor, containing a catalyst as described above, in which a stream is fed containing a water solution of benzene-diols, at concentrations ranging from 5 to 60% by weight, together with a hydrogen stream in such a quantity that the ratio between the total moles of hydrogen and the benzene-diols ranges from 2:1 to 50:1. The feed stock is vaporized and heated to a temperature ranging from 250 to 500° C. and the pressure is kept at a value ranging from 1 to 100 bar. The stream at the reactor outlet consists of the reaction raw material, comprising the possible residual benzene-diols and the phenol produced in water solution, and the residual hydrogen which is recycled.

In a further embodiment of the invention, the reaction is carried out in two or more fixed bed adiabatic reactors in series, with the purpose of cooling the stream at the reactor outlet, before entering the subsequent reactor, so as to limit the temperature increase in each reactor, for example by maintaining it lower than 40° C. In this form of embodiment, both the water and the hydrogen feeding can be partialized to the single reactors. Partialization is particularly useful as it avoids the use of an intermediate heat exchanger for the cooling.

Two reactors are normally sufficient for maintaining the temperature increase inside each reactor within 40° C., thus allowing a higher selectivity to phenol.

The enclosed FIG. 1 schematically shows equipment suitable for the embodiment of the process according to the plant configuration described above.

It is possible to maintain the reactor operating for several hundreds of hours, with the catalysts and under the most suitable operative conditions, with a conversion of benzene-diols and a selectivity to phenol>85%.

If the reactor operation is prolonged, the conversion tends to be reduced, whereas the selectivity remains very high. In this situation, the reaction temperature can be progressively increased within the range of 250-500° C., and the desired conversion degree can be maintained.

The reason for the reduction in activity is the deposit of carbonaceous material on the catalyst during its use in reaction. It has been verified that the catalysts useful for the purposes of the invention can be subjected to periodical regeneration, without any particular problems, according to what is known in the state of the art (temperature of 400÷550° C., pressure of 1÷3 bar, with mixtures of oxygen and nitrogen in a ratio of 0.1÷20% by volume and a space velocity of 3,000÷6,000 $h^{-1}$, as liters of mixture of gas/h/liters of catalyst).

The catalytic composition of the invention based on multicomponent metal oxides comprising at least one metal selected from groups VB, VIB, VIII, IB, IIB, IVA, VA, preferably includes at least one element selected from copper, vanadium, bismuth, molybdenum, niobium, iron, tungsten, zinc, nickel and mixtures thereof, possibly containing antimony and/or phosphorous.

The active phase can be obtained according to the methods known in the state of the art, including precipitation, use of supports, or the use, in any form, of blends of oxides or mixed oxides (M. Campanati, G. Formasari, A. Vaccari, Fundamentals in the preparation of heterogeneous catalysts, Catalysis Today 77 (2003) 299-314).

The active phase is preferably deposited on a support (for ex. alumina, silica, etc.) or formed by using binders and techniques known in the state of the art.

The catalyst can be conveniently formed, for example, by supporting it, by compacting it (for example tableting, extrusion, etc.) or by spray drying, so as to obtain the appropriate forms and dimensions of the catalyst for the specific reaction, according to the methods known in the state of the art. Auxiliary products can be used, when necessary, such as lubricants based on graphite or stearic acid, etc. Solid precursors of the active phase can be conveniently formed even before the final calcination.

The catalyst can also include additional metal ions (doping agents), in order to improve the RedOx, acid base characteristics and the capacity of storing oxygen, such as, for example: metal ions selected from the group consisting of alkaline metals (Na, K) and alkaline earth metals (Mg, Ca, Sr), from the group IVB (preferably Ti, Zr, Hf) and VIIB, from the series of lanthanides (La, Ce, Sm, Gd, Dy, Yb) and from the group of noble metals (for ex. Pt, Pd, Rh, Ru, Ir and blends thereof).

The noble metals can be deposited on the catalyst by means of conventional methods such as impregnation, ion exchange, spray drying, etc., using a solution of a compound of a noble metal. The compounds of noble metals which can be used comprise salts such as halides, nitrates, acetates and sulphates or solutions thereof.

Some specific examples of metal precursors and their solutions, known in the state of the art and easily available on the market include, for example:

Dihydrogen hexachloroplatinate, potassium hexachloroplatinate, tetramineplatinum chloride, tetramineplatinum nitrate, tetramineplatinum hydroxide, palladium bisacetylacetonate, sodium tetrachloropalladiate, tetraminepalladium chloride, rhodium nitrate, rhodium trichloride, ruthenium trichloride, ammonium chloro iridate.

The support treated with the noble metal precursor can be subjected to chemical treatment, possibly alternated with thermal treatment. A typical chemical treatment is, for example, metal reduction, previously impregnated on the support with a Palladium precursor, with a solution of sodium formiate at 85-95° C., according to the state of the art.

The catalysts preferably contain active oxide phases essentially in crystalline form.

Multicomponent metal oxide compositions are particularly preferred, containing at least one crystalline structure, which can be correlated to the scheelite structure.

Crystalline structures which can be correlated to the scheelite structure having the following general compositions, are particularly preferred:

$$Bi_{(1-x/3)}V_{(1-x)w}Nb_{(1-x)(1-w)}Mo_xO_4,$$

$$Cu_{(1-z)}Zn_zW_{(1-y)}Mo_yO_4.$$

A crystalline structure which can be correlated to the scheelite structure refers to a generic $ABO_4$ phase with isomorphic conformation to that present in the Scheelite mineral ($CaWO_4$).

The charge on the various metal ions A and B can be varied, compatibly with the characteristics of crystal electro-neutrality. The generic formula $ABO_4$ can therefore include ternary metal oxides (from $A^{+1}B^{+7}O_4$ to $A^{+4}B^{+4}O_4$) or multicomponent metal oxides whose ionic charge satisfies electro-neutrality requirements.

A description relating to crystalline materials of the scheelite typology can be found in R. W. G. Wyckoff "Crystal Structure" vol. 2, second edition, page VIII a6 and table VIII a5; further indications can be obtained from U.S. Pat. Nos. 3,843,553 and 3,806,470 Aykan et al. (DuPont 1974).

The definition crystalline structure which can be correlated to the scheelite structure therefore also intends to claim those crystallographic variations obtained by means of suitable substitutions of the Ca and W ions of the classical structure. These crystallographic variations imply variations in the arrangement of the atoms in the elementary cell and therefore in its volume.

The use of diffractometric techniques, by experts in the art, allows to detect the presence of crystalline structures, which can be correlated to the scheelite structure, to be revealed.

More specifically, the presence of this crystalline structure can be revealed using the X-ray diffraction (XRD) technique.

The diffraction spectra relating to these crystalline structures can differ from each other, either due to the effect of the different cell volumes or to the effect of isomorphic substitutions; sometimes decreases in the lattice symmetry can also be found.

A Philips X'Pert $\theta/2\theta$ automatic powder diffractometer with a Bragg-Brentano geometry is used for the catalysts mentioned in this patent, using Cu K$\alpha$ X radiation with $\lambda=1,5416$ Å and a power of 1.6 Kw; the angular range used is from 5 to 90° ($2\theta$) with a step size of 0.02° ($2\theta$) and acquisition times of 10 seconds per step.

The scheelite structure can be recognized, by means of XRD, using the various methods known to experts in the field, in particular the information contained in the database PDF-2 (Powder Diffraction File) issued by ICDD® (The International Centre for Diffraction Data®) can be used.

Materials having a scheelite structure or which can be correlated to the same, of the $Bi_{(1-x/3)}V_{(1-x)w}Nb_{(1-x)(1-w)}Mo_xO_4$ type, can be identified by means of diffractograms contained in reference cards such as 14-0688 (BiVO$_4$; x=0, w=1), 85-629 (x=0.21, w=1), 85-630 (x=0.37, w=1), 85-631 (x=0.55, w=1) and 70-0031 (Bi$_3$(FeO$_4$)MoO$_4$)$_2$).

Materials with a scheelite structure, or which can be correlated to this, of the $Cu_{(1-z)}Zn_zW_{(1-y)}Mo_yO_4$ type can be identified by means of crystallograms contained in reference cards such as 88-0269 (Scheelite Cu-exchanged).

The presence of other crystalline phases based on oxides has proved to be extremely advantageous for the production of phenol.

The catalyst can also contain materials with a non-scheelite crystalline or amorphous structure, coming, for example, from some of the precursors used.

The catalyst can also advantageously contain materials, also with a non-scheelite crystalline or amorphous structure, capable of increasing the oxygen storage capacity of the structure (OSC, Oxygen Storage Capacity) such as lanthanide oxides (LnO$_x$), and in particular cerium oxide, or mixtures thereof with other oxides, for example cerium oxide, zirconium oxide.

Typical oxides or blends of oxides can be based on Lanthanum, Cerium, Praseodymium, Neodymium, Europium, Samarium, Gadolinium; Lanthanide oxides (Lanthanides are indicated in short by Ln, their oxides by LnO$_x$) or blends thereof can also be used as a support and/or in the formulation of the binder.

In accordance with what is specified above, the catalyst can consist not only of oxide materials with a scheelite structure;

examples of non-scheelite components can be alkaline or earth alkaline ions, noble metals or compounds thereof under a higher oxidation state or a mixture thereof.

There are no particular restrictions in the catalyst forming methods, due to the versatility of the active phase.

Some illustrative examples, which should in no way be considered as limiting the scope of the invention, are provided hereunder for a better understanding of the present invention and for its embodiment.

EXAMPLES

Examples of Catalyst Preparation

Example 1

Catalyst of the $Bi_{(1-x/3)}V_{(1-x)w}Nb_{(1-x)(1-w)}Mo_xO_4$ Type

A. 7.22 g of ammonium (meta)vanadate [NH$_4$VO$_3$; assay>99.5%; MW 116.98; CAS 7803-55-6] are dissolved, at 80° C., into 450 g of demineralized water and brought to pH 10 by means of ammonium hydroxide at 32% (final weight of the solution 340 g, due to partial evaporation).

B. 17.2 g of bismuth nitrate pentahydrate [(BiNO$_3$)$_3$*5H$_2$O; assay 98%; MW 485.08; CAS 10035-06-0] are dissolved in a solution of 500 g of demineralized water and 5.0 g of a solution of nitric acid at 65%.

C. 195.4 g of the residual 340 g of the solution A are mixed with solution B. The solvent is evaporated at 80° C., with magnetic stirring. The solid product thus obtained is dried in an oven at 120° C. for 18 hrs, then calcined at 500° C. for 4 hrs.

The molar ratio of the reagents is such that:
x=0; w=1 in $Bi_{(1-x/3)}V_{(1-x)w}Nb_{(1-x)(1-w)}Mo_xO_4$.

The XRD spectrum of the material thus obtained has the typical peaks of Clinosbivanite (BiVO$_4$, card 14-0688).

Example 2

Catalyst of the $Bi_{(1-x/3)}V_{(1-x)w}Nb_{(1-x)(1-w)}Mo_xO_4$ Type

A. 4.74 g of niobium chloride [NbCl$_5$; assay 99.8%; MW 270.16] are poured, under magnetic stirring, into a glass containing 50 g of demineralized water. After about 5 minutes, the whole mixture is brought to pH 8 by means of ammonium hydroxide solutions at 32%. The precipitate is filtered and carefully washed with about 500 ml of demineralized water. The solid thus obtained is dissolved, at 90° C., into a solution containing 140 g of demineralized water and 16 g of oxalic acid.

B. A solution is prepared consisting of 5.08 g of ammonium heptamolybdate tetrahydrate [(NH$_4$)$_6$Mo$_7$O$_{24}$*4H$_2$O; assay 81.0÷83.0% (MoO$_3$); MW 1235.86; CAS 12054-85-2] and 2.055 g of ammonium (meta)vanadate (NH$_4$VO$_3$; assay>99.5%; MW 116.97; CAS 7803-55-6) dissolved in 400 g of demineralized water, at 80° C., brought to pH 10 by means of a 32% ammonium hydroxide solution.

The solutions prepared under items A and B are mixed and a third solution is added, consisting of 50 g of demineralized water, 7 g of nitric acid at 65% and 26.35 g of bismuth nitrate pentahydrate [(BiNO$_3$)$_3$*5H$_2$O; assay 98%; MW 485.08; CAS 10035-06-0]. The solvent is evaporated at 120° C. under magnetic stirring. The solid product thus obtained is dried in an oven at 120° C. for 18 hrs, then calcined at 500° C. for 4 hrs.

The molar ratio of the reagents is such that:
x=0.45; w=0.5 in $Bi_{(1-x/3)}V_{(1-x)w}Nb_{(1-x)(1-w)}Mo_xO_4$.

XRD analysis of the material thus obtained shows a crystalline conformation which can be attributed to crystalline structures that are correlated to disorderly scheelite structures such as those, already mentioned, present in mixed oxides of bismuth, iron and molybdenum (for ex. $Bi_3(FeO_4)(MoO_4)_2$, card 70-0031). XRD analysis of the material also shows a crystalline conformation which can be attributed to scheelite structures such as those mentioned in Example 1, Example 3 and Example 4.

Example 3

Catalyst of the $Bi_{(1-x/3)}V_{(1-x)w}Nb_{(1-x)(1-w)}Mo_xO_4$ Type

A solution is prepared consisting of 3.0 g of ammonium heptamolybdate tetrahydrate [$(NH_4)_6Mo_7O_{24}*4H_2O$; assay 81.0÷83.0% ($MoO_3$); MW 1235.86] and 5.38 g of ammonium (meta)vanadate ($NH_4VO_3$; assay>99.5%; MW 116.97) dissolved in 400 g of demineralized water, at 80° C., brought to pH 10 by means of a 32% ammonium hydroxide solution. A solution is added, consisting of 60 g of demineralized water, 6 g of nitric acid at 65% and 27.83 g of bismuth nitrate pentahydrate [$(BiNO_3)_3*5H_2O$; assay 98%; MW 485.07]. The solvent is evaporated at 80° C. under magnetic stirring. The solid product thus obtained is dried in an oven at 120° C. for 66 hrs, and then calcined at 500° C. for 4 hrs.

The molar ratio of the reagents is such that:
x=0.27; w=1 in $Bi_{(1-x/3)}V_{(1-x)w}Nb_{(1-x)(1-w)}Mo_xO_4$.

XRD analysis of the material thus obtained shows a crystalline conformation which can be attributed to scheelite structures such as those appearing in the cards 14-0688 ($BiVO_4$; x=0, w=1), 85-629 (x=0.21, w=1), 85-630 (x=0.37, w=1), 85-631 (x=0.55, w=1).

Example 4

Catalyst of the $Bi_{(1-x/3)}V_{(1-x)w}Nb_{(1-x)(1-w)}Mo_xO_4$ Type

A solution is prepared consisting of 5.08 g of ammonium heptamolybdate tetrahydrate [$(NH_4)_6Mo_7O_{24}*4H_2O$; assay 81.0÷83.0% ($MoO_3$); MW 1235.85] and 4.11 g of ammonium (metha)vanadate ($NH_4VO_3$; assay>99.5%; MW 116.97) dissolved in 400 g of demineralized water, at 80° C., brought to pH 10 by means of a 32% ammonium hydroxide solution. A solution is added, consisting of 60 g of demineralized water, 6 g of nitric acid at 65% and 26.35 g of bismuth nitrate pentahydrate [$(BiNO_3)_3*5H_2O$; assay 98%; MW 485.07]. The solvent is evaporated at 80° C. under magnetic stirring. The solid product thus obtained is dried in an oven at 120° C. for 18 hrs, and then calcined at 500° C. for 4 hrs.

The molar ratio of the reagents is such that:
x=0.45; w=1 in $Bi_{(1-x/3)}V_{(1-x)w}Nb_{(1-x)(1-w)}Mo_xO_4$.

XRD analysis of the material thus obtained shows a crystalline conformation which can be attributed to scheelite structures such as those appearing in the cards 14-0688 ($BiVO_4$; x=0, w=1), 85-629 (x=0.21, w=1), 85-630 (x=0.37, w=1), 85-631 (x=0.55, w=1).

Example 5

Catalyst of the $Cu_{(1-z)}Zn_zW_{(1-y)}Mo_yO_4$ Type

A solution is prepared consisting of 60.15 g of copper sulphate pentahydrate ($CuSO_4*5H_2O$; assay>99%; MW 249.68; CAS 7758-99-8) in 1,500 g of demineralized water and the solution is brought to boiling point. A second solution is added, prepared by dissolving 115 g of sodium tungstate dihydrate ($Na_2WO_4*2H_2O$; assay>99%; MW 329.85; CAS 10213-10-2) in 1,150 g of demineralized water. The suspension is stirred for 5 hours at 50° C. and is left to rest for a night at room temperature. The solid is separated by filtration and is washed with about 5 litres of demineralized water. The solid is dried in an oven at 120° C. for 15 h and calcined at 600° C. for 48 h.

XRD analysis of the material thus obtained shows a crystalline conformation compatible with exchanged scheelite structures such as that appearing in the card 88-0269 Scheelite (Cu-exchanged)-$Cu(WO_4)$. In order to limit the formation of phases of the CuO type, precipitation with a deficiency of Cu ions was preferred.

Example 6

Catalyst of the $Cu_{(1-z)}Zn_zW_{(1-y)}Mo_yO_4/LnO_x$ Type

A solution is prepared, consisting of 24.42 g of ammonium para-tungstate [$(NH_4)_{10}W_{12}O_{41}*H_2O$; assay 99.99%; MW 3060, 46; CAS 11120-25-5] and 400 g of demineralized water, stirring at 70° C. A second solution is prepared by dissolving 22.4 g of copper nitrate trihydrate ($Cu(NO_3)_2$$_3H_2O$; >99%; MW 241.60; CAS 10031-43-3) and 8.995 g of Cerium Nitrate hexahydrate ($CeN_3O_9*6H_2O$; 99%; MW 434.22; CAS 10294-41-4) in 150 g of demineralized water. The two solutions are joined and dried by heating to 120° C., under stirring.

The mixture is dried at 120° C. for 15 h and is calcined at 600° C. for 48 h.

XRD analysis of the material thus obtained shows a crystalline conformation compatible with exchanged scheelite structures such as that appearing in the card 88-0269, Scheelite (Cu-exchanged)-$Cu(WO_4)$.

It should be noted that due to hydration phenomena, the copper titre of the copper nitrate precursor should be considered as being approximately 15% lower than the content of the commercial product.

Example 7

Catalyst of the $Cu_{(1-z)}Zn_zW_{(1-y)}Mo_yO_4$ Type

A solution is prepared, consisting of 9.015 g of copper sulfate pentahydrate ($CuSO_4*5H_2O$; assay>99%; MW 249.68; CAS 7758-99-8) and 2.18 g of Zinc sulfate monohydrate (($ZnSO_4*H_2O$; assay>97.5%; MW 179.45; CAS 7446-19-7) in 300 g of water. The mixture is brought to boiling point, and 230 g of a sodium tungstate solution 10% in water (CAS 10213-10-2) are then added. The mixture is cooled to 50° C. and is kept at this temperature for 4 h. The precipitate is aged for a night at room temperature, filtered, washed, dried at 120° C. for 15 h and calcined at 600° C. for 48 h.

For the purposes of the present invention, typical oxidation and reduction catalysts of the known art can be adopted, as useful comparative examples.

Example 8

Comparative

A typical oxidation example, in particular using a "RedOx technology" approach, is described by R. M. Contractor et al. in Catalysis Today, 1 (1987) 49-58 for the oxidation of butane to maleic anhydride with VPO catalysts. As already mentioned above, this process is one of the RedOx technologies, as defined in the present patent, which has reached one of the highest advancement states on an industrial scale. The synthesis of an active phase following a similar procedure to that described in the above article, is described herein.

90 ml of isobutylic alcohol and 60 ml of benzylic alcohol are charged into a glass flask, and 15 g of vanadium pentoxide ($V_2O_5$; assay>99.6+%; MW 181.88; CAS 1314-62-1) are added. The mixture is heated in a heating bath, refluxed for 6 hours at 130° C., and then left to rest for a night at room temperature. 21.8 g of phosphoric acid ($H_3PO_4$; titre 85%; CAS 766-38-2) are subsequently added and the mixture is heated to 130° C., at reflux, for a further 4 h. After cooling, the product is filtered and dried in the air for 15 h at 120° C. Part of the dried sample is calcined at 400° C. for 4 h in air.

As indicated in the above article, for optimum catalysts, it is essential to prepare the crystalline phase $(VO)_2P_2O_7$ by means of the precursor $(VO)_2H_2O(PO_{30}H)_2$: these two phases were identified, by means of X-ray diffraction, in the calcined sample and in the dried sample, respectively.

Example 9

Comparative

For the purposes of the present invention, reduction catalysts available on the market can be adopted as useful comparative examples. Copper-based catalysts supported on alumina can be used, for example, such as the catalyst T4489 produced and commercialized by Süd-Chemie Inc., whose description can be found in the technical-commercial literature provided by the producer.

Examples of Catalytic Performances

Hydroxylation of Benzene: Experimental Technique of the Catalytic Test

The use of a catalytic test system which allows an efficient, economical and systematic study for the optimum reaction conditions of each catalyst, represents, for the reaction in question, a significant improvement with respect to the current state of the art. In this sense, the primary objective of rapidly comparing numerous catalysts within a wide variety of reaction conditions can be privileged with respect to the quantitative accuracy. In a test under depletive conditions, wherein the oxidation state of the catalyst is continuously evolving, the rapidity of the measurement test is fundamental for an accurate description of the catalytic performances.

The mass spectroscopy technique (MS) is well-known for its fast analytical properties and great sensitivity towards the identification of by-products, above all for samples with a relatively limited number of chemical species contemporaneously present.

Mass spectrometers commercially available allow components to be detected at approximately one part per million (1 ppm) and can reach, also in the case of economical models, up to about ten parts per billion (10 ppb=0.01 ppm). Furthermore, by coupling the mass spectrometer with a reactor operating at a temperature and flow controlled and modifiable with the tests underway, it is possible to study a wide range of operating conditions for each catalyst: 1÷60 masses (selected) per second can normally be analyzed, with more sophisticated instruments even 100 masses/s can be reached and exceeded. For these reasons, the mass spectrometer is widely used in cases in which a combined approach, or assimilable, experimental typology, is required, coupled with the necessity of also being able to detect low concentrations of the desired product and possible byproducts (for example U.S. Pat. Nos. 6,440,745- 6,316,616-6,323,366).

By well adapting itself to the demands of this research, the mass spectrometer (MS) allows a rapid and sufficiently accurate estimation of the selectivity of the catalytic process, referring to the maximization of the desired product and minimization of the by-products.

With the approach used, for each catalyst, it is possible to modify numerous operating conditions (for example, temperature, contact time, partial pressure, oxidation state of the catalyst, etc.) and the results can be evaluated in real time during the reaction.

The instrumentation used is thus defined as TTPC-MS (Temperature and Time Programmed Chemistry-Mass Spectrometry).

Hydroxylation of Benzene: Operating Procedure of the Catalytic Test

Unless expressly indicated, the results refer to tests carried out under standard conditions, as described below.

The reaction is carried out, in vapour phase, in a fixed U-bed reactor (material=quartz, total length=320 mm), whose two branches have different internal diameters to obtain both an efficient preheating of the feed and also a rapid transfer, without remixing, of the products to the spectrometer (feeding zone: $\emptyset_{int}$=4.0 mm, length=120 mm; product desorption zone: $\emptyset_{int}$=1.2 mm). The reactor is equipped with an outer side sheath close to the catalyst, with a thin thermocouple ($\emptyset_{ext}$=0.5 mm) of the K type.

The reactor is placed in a tubular oven with electric heating controlled by a temperature programmer.

The catalyst charge is generally 0.2 g, it has a size of 42-80 mesh and is positioned on a quartz wool layer.

The catalyst is initially maintained in a stream of 25 ml/min of inert gas (generally $N_2$, in some cases He) at 120° C. for at least two hours.

At the end of this phase, a further stream of $N_2$ is fed (usually 25 ml/min, but it can be varied, possibly also during the test), previously bubbled into benzene (generally maintained at 25° C., but the temperature can also be optionally varied during the test to change the partial benzene pressure).

Under these conditions (25 ml/min of $N_2$ bubbled into benzene at 25° C.), with the saturation system used, about 0.7 grams of benzene are fed for each hour of the test, obtaining a partial pressure of 0.06, consequently a GHSV=44,000 $h^{-1}$ (Gas Hourly Space Velocity, expressed in terms of litres of gas passed through the reactor per litre of catalyst per hour), if calculated at the reaction temperature of 550° C. and considering an average bulk density of catalysts of 1 g/ml), contact time=0.08 s, WHSV=22 $h^{-1}$ (calculated, as defined above, with respect to the whole feeding mixture per gram of catalyst per hour).

Under the conditions described, the signal corresponding to the Atomic Mass Unit 78 (AMU 78), which can be attributed to the benzene molecular ion, fed without reaction, has, in all tests Ionic Current values (I.C.) of 3.0E-7>I.C.>1.5E-7. Partial benzene pressures equal to 0.06, corresponding to benzene concentrations in gas phase of 6% (vol/vol), can be associated with these ionic current values.

The heating of the reactor from a temperature of 120° C. to the maximum measurement temperature, generally 550° C., takes place with an increase of 11° C./min, a constant temperature is subsequently maintained.

The analyses are carried out on the gas phase, in continuous, both during the heating and during the isotherm. Due to the depletive approach (deficiency/lack of oxidants in gas phase), the time and reaction rate, at a certain temperature, contribute to determining the oxidation state of the catalyst; the surface oxidation state of the catalyst is particularly important for the purposes of the reactivity.

The product analysis is carried out with two different sensitivities: scanning from 1 to 80 AMU, amplifier range of the Ionic Current intensity (a.b.I.C.) of 1E-6 AMPS and scanning from 1 to 180 AMU, with a a.b.I.C. of 1E-9 AMPS. This procedure method (contemporaneous scanning at different sensitivities) should be considered as being decisive for identifying products which are not visible at a low sensitivity. The analysis method described allow a complete scanning to be effected for each minute of analysis.

In this way, a complete scanning, with temperature ramp, is carried out with approximately each 11° C. The test then continues isothermally, registering up to 300 pairs of spectra.

The analysis is carried out with continuous on line sampling directly on the gas phase, without chromatographic separation.

The line after the reactor is heated to a constant temperature of 120° C. The residual pressure of the line is controlled by means of a Pirani-Penning measurement unit.

The spectrometer MS and the final part of the line are evacuated using the two-step turbo-molecular pump of the spectrometer itself, up to a residual pressure of 1 torr in the sampling chamber and about $6.1 \cdot 10^{-6}$ torr in the mass spectrometer MS. The measurement instrument is a mass spectrometer model Thermostar supplied by BALZERS. The data management program is supplied by the constructor and allows up to 63 masses selected over a period of time (or up to 300 masses in continuous scanning) to be monitored and acquired. The mass spectrum thus indicates all the peaks, fundamental and fragmentations, of the reaction products and non-converted reagents. The identification of the compounds of major interest, i.e. benzene (Atomic Mass Unit AMU 78, 51, 52, 50, 39, 63, 77), phenol (AMU 94, 66), carbon dioxide (AMU 44, 28 and water (AMU 18,17) is sufficiently reliable, as the fragmentations are not superimposed. The substantial non-superimposition of the peaks allows to avoid optimisation methods of the square minima on the matrix of the I.C., to identify the I.C. portions of each single peak, belonging to different compounds.

In our case, which should be considered an exception, the products are correctly correlated to a single I.C., or pair of I.C. Phenol is recognized, for example, and semiquantitatively estimated from the I.C. of AMU 94, possibly validated by the I.C. value of AMU 66. Other reaction byproducts are maleic anhydride (AMU 26, 54, 28, 98), cyclohexenone (AMU 68, 96), dibenzofuran (168, 139, 84) and benzofuran (118, 89).

All the compounds were confirmed by GC-MS on medium fractions of condensate from the carrier gas leaving the reactor.

The intensity of each AMU is proportional to the quantity of fragment referred to and is, in final analysis, once known the relative intensity of the fragmentation peaks typical of the product in question, proportional to the partial pressure/concentration of the product in the gas phase analyzed.

For all the molecules considered, the molecular ion proves to be that characterized by a greater intensity, with the exception of maleic anhydride for which the ion at AMU 26 is preferred to the molecular ion (Percent Relative Abundance, RA % AMU 98≈8).

For the molecules considered, with the exception of maleic anhydride already mentioned, the intensity of the molecular ion can be directly correlated, semiquantitatively, to the concentration of the product in the gaseous mixture.

The determination of the relative concentrations is however of a semi-quantitative nature due to uncertainties and non-homogeneity relating to factors, known in the state of the art, such as ionisation efficiency, jet separator effect (the sampling system tends to enrich the mixture to be analyzed in heavy products), etc., which are difficult to quantify for a more accurate determination in the complex gas mixture considered.

The regeneration of the catalyst after the catalytic activity experiment is effected in the same reactor used for the reaction, without removing the catalyst. The operating conditions are as follows: temperature ranging from 350 to 550° C., pressure=1-1.2 bar, oxygen concentration=0.1-20% and GHSV space velocity=10000÷50000 h$^{-1}$. In particular, the treatment is activated with a stream of nitrogen alone, to which an equal flow of air is progressively added (in about 1 hour), the nitrogen flow is subsequently progressively reduced unit it is annulled (in about 1 hour). The treatment is prolonged for 1 to 10 hours. At the end of the regeneration treatment the reactor is washed with nitrogen for 5 minutes at the same temperature and is then cooled under a flow to 120° C., after which the reaction cycle can be restarted, in a depletive environment as described above.

The catalysts tested proved to be stable to at least twelve reaction and regeneration cycles.

For the reasons discussed above, the catalytic data should be considered semi-quantitative, and consequently Examples 10-20 indicate the activity data expressed as an I.C. value for a certain temperature (corresponding to a certain measurement cycle); the catalytic performances are estimated however by calculating the benzene conversion and selectivity to phenol according to the following formulae.

For Conversion>10%

The difference between the signal intensity of the benzene in the presence and absence of a reaction is significant and therefore:

$$\text{Conversion \%}=C\%=[(\text{I.C. AMU 78 in})-(\text{I.C. AMU 78 out})]/(\text{I.C. AMU 78 in})$$

$$\text{Yield \%}=Y\%=100*(\text{I.C. AMU 94})/(\text{I.C. AMU 78 in})$$

$$\text{Selectivity \%}=S\%=100*Y\%/C\%$$

wherein:
(I.C. AMU 78 in)=atomic mass ionic current 78 (benzene) without reaction,
(I.C. AMU 78 out)=atomic mass ionic current 78 (benzene) with reaction,
(I.C. AMU 94)=atomic mass ionic current 94 (phenol produced).

For Conversion<10%

The conversion values are low and cannot therefore be estimated from the difference of intensities of the peak characteristic of the reagent with or without reaction; when the combustion products are, in addition to phenol, the only products formed in a significant quantity, the conversion is determined by the carbon dioxide

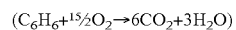
$(C_6H_6+15/2 O_2 \rightarrow 6CO_2+3H_2O)$ and by the phenol

$(C_6H_6+1/2 O_2 \rightarrow C_6H_5OH)$.

The typical reactivity values are therefore estimated as follows:

$$\text{Conversion \%}=C\%=100*[(\text{I.C. AMU 94})+(\text{I.C. AMU 44})/6]/(\text{I.C. AMU 78 in})$$

wherein: (I.C. AMU 44)=atomic mass ionic current unit 44 (carbon dioxide produced).

Yield % and Selectivity % are estimated as in the previous case.

Examples 10-20

The examples described were carried out according to the procedure illustrated above. The estimation of the parameters such as Conversion, Selectivity and Yield are effected as described in the previous item.

The operating conditions adopted and the catalytic performances estimated are specified in the tables.

Example 10

| Catalyst | |
|---|---|
| Type of catalyst | BiVNbMo |
| Preparation catalyst (see) | Example 2 |
| Operative conditions | |
| Measurement temperature ° C. (cycle number) | 550 (49) |
| WHSV ($h^{-1}$) ($\alpha$) | 22; (3.5) |
| Catalytic performances | |
| AMU 78 fed amps (E-10) ($\beta$) | 2600 |
| AMU 94 amps (E-10) ($\chi$) | 0.44 |
| AMU 44 amps (E-10) ($\chi$) | 270 |
| AMU 78 amps (E-10) ($\chi$) | 2600 |
| Estimated yield % | 0.02 |
| Estimated conversion % | 2 |
| Estimated selectivity % | 1 |

Notes:
$\alpha$ = WHSV [g/h benz. + g/h $N_2$]/g cat.; [g/h benz.]/g cat
$\beta$ = ionic current in the absence of reaction
$\chi$ = ionic current in the presence of reaction

Example 11

| Catalyst | |
|---|---|
| Type of catalyst | BiVMo |
| Preparation catalyst (see) | Example 3 |
| Operative conditions | |
| Measurement temperature ° C. (cycle number) | 550 (80) |
| WHSV ($h^{-1}$) ($\alpha$) | 22; (3.5) |
| Catalytic performances | |
| AMU 78 fed amps (E-10) ($\beta$) | 2500 |
| AMU 94 amps (E-10) ($\chi$) | 0.32 |
| AMU 44 amps (E-10) ($\chi$) | 120 |
| AMU 78 amps (E-10) ($\chi$) | 2500 |
| Estimated yield % | 0.01 |
| Estimated conversion % | 1 |
| Estimated selectivity % | 2 |

Notes:
see notes of Example 10

Example 12

| Catalyst | |
|---|---|
| Type of catalyst | BiVMo |
| Preparation catalyst (see) | Example 4 |
| Operative conditions | |
| Measurement temperature ° C. (cycle number) | 550 (100) |
| WHSV ($h^{-1}$) ($\alpha$) | 22; (3.5) |
| Catalytic performances | |
| AMU 78 fed amps (E-10) ($\beta$) | 2300 |
| AMU 94 amps (E-10) ($\chi$) | 0.37 |
| AMU 44 amps (E-10) ($\chi$) | 65 |
| AMU 78 amps (E-10) ($\chi$) | 2300 |
| Estimated yield % | 0.02 |
| Estimated conversion % | 0.5 |
| Estimated selectivity % | 3 |

Notes:
see notes of Example 10

Example 13

The effect is shown of the variation in the space velocity, with respect to the test indicated in Example 12

| Catalyst | |
|---|---|
| Type of catalyst | BiVMo |
| Preparation catalyst (see) | Example 4 |
| Operative conditions | |
| Measurement temperature ° C. (cycle number) | 550 (70) |
| WHSV ($h^{-1}$) ($\alpha$) | 690; (35.0) |
| Catalytic performances | |
| AMU 78 fed amps (E-10) ($\beta$) | 2900 |
| AMU 94 amps (E-10) ($\chi$) | 0.28 |
| AMU 44 amps (E-10) ($\chi$) | 23 |
| AMU 78 amps (E-10) ($\chi$) | 2900 |
| Estimated yield % | 0.01 |
| Estimated conversion % | 0.1 |
| Estimated selectivity % | 7 |

Notes:
see notes of Example 10

Example 14

| Catalyst | |
|---|---|
| Type of catalyst | $CuWO_4$ |
| Preparation catalyst (see) | Example 5 |
| Operative conditions | |
| Measurement temperature ° C. (cycle number) | 530 (47) |
| WHSV ($h^{-1}$) ($\alpha$) | 22; (3.5) |
| Catalytic performances | |
| AMU 78 fed amps (E-10) ($\beta$) | 1800 |
| AMU 94 amps (E-10) ($\chi$) | 4.3 |
| AMU 44 amps (E-10) ($\chi$) | 340 |
| AMU 78 amps (E-10) ($\chi$) | 1700 |
| Estimated yield % | 0.1 |
| Estimated conversion % | 3 |
| Estimated selectivity % | 3 |

Notes:
see notes of Example 10

Example 15

This shows the stability to RedOx cycles. The catalyst used is that prepared in Example 5, but subjected to 12 reaction-regeneration cycles. Within the limits of the semi-quantitative analysis effected, no irreversible deterioration of the catalyst is observed.

Example 16

| Catalyst | |
|---|---|
| Type of catalyst | CuWO$_4$ after 12 RedOx cycles |
| Preparation catalyst (see) | Example 5 after 12 RedOx cycles |
| Operative conditions | |
| Measurement temperature ° C. (cycle number) | 530 (53) |
| WHSV (h$^{-1}$) ($\alpha$) | 22; (3.5) |
| Catalytic performances | |
| AMU 78 fed amps (E-10) ($\beta$) | 1900 |
| AMU 94 amps (E-10) ($\chi$) | 2.6 |
| AMU 44 amps (E-10) ($\chi$) | 115 |
| AMU 78 amps (E-10) ($\chi$) | 1780 |
| Estimated yield % | 0.14 |
| Estimated conversion % | 1 |
| Estimated selectivity % | 12 |

Notes:
see notes of Example 10

Example 17

| Catalyst | |
|---|---|
| Type of catalyst | Cu$_{0.75}$Zn$_{0.25}$WO$_4$ |
| Preparation catalyst (see) | Example 7 |
| Operative conditions | |
| Measurement temperature ° C. (cycle number) | 530 (41) |
| WHSV (h$^{-1}$) ($\alpha$) | 22; (3.5) |
| Catalytic performances | |
| AMU 78 fed amps (E-10) ($\beta$) | 2250 |
| AMU 94 amps (E-10) ($\chi$) | 2.1 |
| AMU 44 amps (E-10) ($\chi$) | 148 |
| AMU 78 amps (E-10) ($\chi$) | 2180 |
| Estimated yield % | 0.09 |
| Estimated conversion % | 1 |
| Estimated selectivity % | 8 |

Notes:
see notes of Example 10

| Catalyst | |
|---|---|
| Type of catalyst | CuWO$_4$ + Ce |
| Preparation catalyst (see) | Example 6 |
| Operative conditions | |
| Measurement temperature ° C. (cycle number) | 480 (42) |
| WHSV (h$^{-1}$) ($\alpha$) | 22; (3.5) |
| Catalytic performances | |
| AMU 78 fed amps (E-10) ($\beta$) | 1800 |
| AMU 94 amps (E-10) ($\chi$) | 5.1 |
| AMU 44 amps (E-10) ($\chi$) | 180 |
| AMU 78 amps (E-10) ($\chi$) | 1650 |
| Estimated yield % | 0.3 |
| Estimated conversion % | 2 |
| Estimated selectivity % | 15 |

Notes:
see notes of Example 10

FIG. 2 shows the trend of the masses from AMU 90 to AMU 120 in relation to the measurement cycle of the experiment. The tendency to give a maximum of phenol production is shown, this is a typical trend for the reactions in depletive conditions.

Example 18

This shows the stability to RedOx cycles. The catalyst used is that prepared in Example 6, but subjected to one reaction-regeneration cycle. Within the limits of the semi-quantitative analysis effected, no irreversible deterioration of the catalyst is observed.

The variation in selectivity is also shown, in relation to the oxidation state of the catalyst. A comparison is made of the data obtained at 34$^{th}$ and at the 60$^{th}$ cycle of MS analysis, corresponding to about 30' of reaction under isotherm regime conditions at 407° C. These values can be correlated with a decreasing in the average oxidation state of the catalyst.

| Catalyst | | |
|---|---|---|
| Type of catalyst | CuWO$_4$ + Ce | |
| Preparation catalyst (see) | Example 6 after one RedOx cycle | |
| Operative conditions | | |
| Measurement temperature ° C. (cycle number) | 407 (34) | 407 (60) |
| WHSV (h$^{-1}$) ($\alpha$) | 22; (3.5) | |
| Catalytic performances | | |
| AMU 78 fed amps (E-10) ($\beta$) | 1940 | 1940 |
| AMU 94 amps (E-10) ($\chi$) | 3.2 | 1.9 |
| AMU 44 amps (E-10) ($\chi$) | 123 | 20 |
| AMU 78 amps (E-10) ($\chi$) | 1700 | 1790 |
| Estimated yield % | 0.2 | 0.1 |
| Estimated conversion % | 1 | 0.3 |
| Estimated selectivity % | 14 | 36 |

Notes:
see notes of Example 10

FIG. 3 indicates the trends of the mass values corresponding to benzene (AMU 78), phenol (AMU 94) and CO$_2$ (AMU 44) during the heating and isotherm at 407° C. The variation in the spectrum of the products during the isotherm at 407° C. indicates the possible existence of surface, or average, oxidation states of the catalyst which appear optimum for the desired reaction.

Comparative Example 19

In this case, conversion, selectivity and yield to maleic anhydride are estimated according to formulae, comparable to those used above:

$$\text{Conversion \%} = C\% = 100*[(I.C. \text{ AMU } 98)*(1000/81) + (I.C. \text{ AMU } 94)] + (I.C. \text{ AMU } 44)/6]/(I.C. \text{ AMU } 78)$$

$$\text{Yield \%} = Y\% = 100*(I.C. \text{ AMU } 98)*(1000/81)/(I.C. \text{ AMU } 78)$$

$$\text{Selectivity \%} = S\% = 100*Y\%/C\%$$

In the semi-quantitative estimation, of yield and selectivity for maleic anhydride, a multiplicative factor equal to 1000/81 is used, as the molecular peak of maleic anhydride is not the most intense and is about 8.1% of the most intense peak at AMU 26 (NITS, National Institute of Standards Technology, Mass Spectral Search Program for the NIST Mass Spectral Library, MS Windows Version 1.6d, built Jul. 27, 1998). It is preferable not to use the peak at AMU 26 as this undergoes strong interference on the part of nitrogen (AMU 28) used as carrier gas.

FIG. 4 indicates the trends of maleic anhydride (AMU 98), phenol (AMU 94), $CO_2$ (AMU 44) and benzene (AMU 78) masses, during the heating and isotherm at 550° C.

| Catalyst | |
|---|---|
| Type of catalyst | VPO |
| Preparation catalyst (see) | Example 8 |
| Operative conditions | |
| Measurement temperature ° C. (cycle number) | 550 (43) |
| WHSV ($h^{-1}$) ($\alpha$) | 22; (3.5) |
| Catalytic performances | |
| AMU 78 fed amps (E-10) ($\beta$) | 3000 |
| AMU 94 amps (E-10) ($\chi$) | 0.145 |
| AMU 98 amps (E-10) ($\chi$) | 1.29 |
| AMU 44 amps (E-10) ($\chi$) | 130 |
| AMU 78 amps (E-10) ($\chi$) | 2950 |
| Estimated yield % | 0.005 |
| Estimated conversion % | 1.3 |
| Estimated selectivity % | 0.7 |
| Estimated yield % to Maleic anhydride | 0.5 |
| Estimated selectivity % to Maleic anhydride | 40 |

Notes:
see notes of Example 10

This example shows that a typical oxidation catalyst, in particular suitable for the RedOx technology (production of maleic anhydride), leads to oxidation products which are different from the desired product (phenol).

Comparative Example 20

| Catalyst | |
|---|---|
| Type of catalyst | $CuO$—$Al_2O_3$ (Süd Chemie T4489) |
| Preparation catalyst (see) | Example 9 |
| Operative conditions | |
| Measurement temperature ° C. (cycle number) | 400 (25) |
| WHSV ($h^{-1}$) ($\alpha$) | 22; (3.5) |
| Catalytic performances | |
| AMU 78 fed amps (E-10) ($\beta$) | 2000 |
| AMU 94 amps (E-10) ($\chi$) | 0.0 |
| AMU 44 amps (E-10) ($\chi$) | 9000 |
| AMU 78 amps (E-10) ($\chi$) | 100 |
| Estimated yield % | 0 |
| Estimated conversion % | 99 |
| Estimated selectivity % | 0 |

This example shows that a typical hydrogenation catalyst, under the operating conditions used for the process, leads to the almost total combustion of the organic compounds involved.

Examples of Catalytic Performances
Hydrodeoxygenation of Benzene-Diols: Operating Procedure of the Catalytic Test The catalytic tests described in the examples were carried out in experimental laboratory equipment, in which it is possible to study the operating conditions to be adopted for the best running mode of the test. The equipment and operating procedure are described hereunder.

The reaction is carried out in vapour phase and under pressure in a tubular fixed bed reactor (material=AISI 316L stainless steel, length 180 mm, $\varnothing_{int}$=11.5 mm, axial sheath for thermocouple with $\varnothing_{ext}$=3 mm).

The reactor is placed in a tubular oven with electric heating.

The catalyst charge is 5.0 g, it has a size of <2 mm and is positioned in the reactor between two layers of granular quartz.

The reactor has a down flow configuration. The aqueous solution of benzene-diols is fed with a dosage pump of the HPLC type and is preheated before introduction into the upper part of the reactor; the solution is then vaporized and mixed with hydrogen directly in the reactor, in the quartz layer situated before the catalyst where it reaches the reaction temperature before coming in contact with the catalyst.

The hydrogen flow-rate is regulated with a thermal mass flow meter.

The pressure of the plant is controlled by a regulation valve situated at the outlet of the reactor.

In the activation phase, the catalyst is heated to the reaction temperature in a flow of hydrogen, at the pressure and flow-rate established for the experiment, and maintained under this condition for 1 hour. The feeding of water is subsequently started at the flow-rate established for the experiment and after 30 minutes, the water is substituted with the solution of benzene-diols.

The mixture of effluent vapours from the pressure regulation valve is condensed and the reaction raw material collected. The condensed raw material normally appears separated into two phases, organic and aqueous, both containing phenol. For the gas chromatographic analysis, the two phases are diluted and mixed with a common solvent, generally tert-butyl alcohol and an internal standard, normally n-octanol is added.

The regeneration of the catalyst after the catalytic activity experiment is effected in the same reactor used for the reaction, without removing the catalyst itself. The operating conditions are as follows: temperature: 450-550° C., pressure=1-3 bar, oxygen concentration=0.1-20% and GHSV space velocity=3000÷6000 $h^{-1}$. In particular, the treatment is started with a flow of nitrogen alone, to which an equal flow of air is progressively added (in about 1 hour), the nitrogen flow is then progressively reduced until annulment (in about 1 hour). The treatment is prolonged for 5 to 10 hours. At the end of the regeneration treatment the reactor is washed with a flow of nitrogen and the hydrodeoxygenation reaction can be restarted.

Hydrodeoxygenation of Benzene-Diols: Conversion and Selectivity Calculation

The catalytic performances are evaluated by calculating the conversion of benzene-diols and the selectivity to phenol according to the formulae:

$$BD \text{ conversion} = 100 * \frac{(1.2 \ BD_{in} + 1.4 \ BD_{in}) - (1.2 \ BD_{out} + 1.4 \ BD_{out})}{(1.2 \ BD_{in} + 1.4 \ BD_{in})}$$

$$\text{Phenol selectivity} = 100 * \frac{Phenol_{out}}{(1.2 \ BD_{in} + 1.4 \ BD_{in}) - (1.2 \ BD_{out} + 1.4 \ BD_{out})}$$

wherein:
BD=benzene-diols
1,2 BD=concentration of 1,2-benzene-diol
1,4 BD=concentration of 1,4-benzene-diol
in=inlet
out=outlet Examples 21-32

The examples provided were carried out according to the procedure illustrated above.

The operating conditions adopted and the catalytic performances are indicated in the following tables.

Example 21

| Catalyst | |
|---|---|
| Type of catalyst | BiVNbMo |
| Preparation catalyst (see) | Example 2 |
| Operative conditions | |
| Reaction temperature (° C.) | 400 |
| Pressure (bar) | 25 |
| Solvent of BDs fed | water |
| 1,2-BD in BD solution (w %) | 19.5 |
| 1,4-BD in BD solution (w %) | 9.8 |
| $H_2$/BD ratio (molar ratio) | 21.2 |
| WHSV ($h^{-1}$) ($\alpha$) | 2.0 |
| Catalytic performances | | |
| T.O.S. (h) ($\beta$) | 5 | 156 |
| Benzenediols conversion (%) ($\delta$) | 100.0 | 98.1 |
| Selectivity to Phenol (%) ($\epsilon$) | 94.0 | 91.1 |

Notes:
BD = benzenediols in general
1,2-BD = 1,2-benzenediol (catechol)
1,4-BD = 1,4-benzenediol (hydroquinone)
$\alpha$ = WHSV, referring to the benzenediols fed
$\beta$, $\gamma$ = time on stream, working hours from the beginning of test ($\beta$) or from the last regeneration effected in the reactor ($\gamma$)
$\delta$ = conversion referring to the sum 1,2-BD + 1,4-BD
$\epsilon$ = selectivity referring to the total converted BDs

Example 22

| Catalyst | |
|---|---|
| Type of catalyst | BiVMo |
| Preparation catalyst (see) | Example 3 |
| Operative conditions | |
| Operative conditions as in Example 21 | |
| Catalytic performances | | |
| T.O.S. (h) ($\gamma$) | 1 | 45 |
| Benzenediols conversion (%) ($\delta$) | 98.0 | 91.6 |
| Selectivity to Phenol (%) ($\epsilon$) | 89.6 | 86.6 |

Notes:
see notes in Example 21

Example 23

| Catalyst | |
|---|---|
| Type of catalyst | BiVO$_4$ |
| Preparation catalyst (see) | Example 1 |
| Operative conditions | |
| Reaction temperature (° C.) | 400 |
| Pressure (bar) | 25 |
| Solvent of BDs fed | water |
| 1,2-BD in BD solution (w %) | 19.3 |
| $H_2$/BD ratio (molar ratio) | 28.0 |
| WHSV ($h^{-1}$) ($\alpha$) | 1.3 |
| Catalytic performances | | |
| T.O.S. (h) ($\gamma$) | 5 | 50 |
| Benzenediols conversion (%) | 99.9 | 96.0 |
| Selectivity to Phenol (%) | 89.6 | 95.3 |

Notes:
see notes in Example 21

Example 24

| Catalyst | |
|---|---|
| Type of catalyst | BiVO$_4$ |
| Preparation catalyst (see) | Example 1 |
| Operative conditions | |
| Reaction temperature (° C.) | 450 |
| Pressure (bar) | 25 |
| Solvent of BDs fed | water |
| 1,2-BD in BD solution (w %) | 19.3 |
| $H_2$/BD ratio (molar ratio) | 28.0 |
| WHSV ($h^{-1}$) ($\alpha$) | 1.3 |
| Catalytic performances | | |
| T.O.S. (h) ($\gamma$) | 5 | 71 |
| Benzenediols conversion (%) | 100 | 96.8 |
| Selectivity to Phenol (%) | 93.0 | 98.7 |

Notes:
see notes in Example 21

Example 25

| Catalyst | |
|---|---|
| Type of catalyst | CuWO$_4$ |
| Preparation catalyst (see) | Example 5 |
| Operative conditions | |
| Reaction temperature (° C.) | 450 |
| Pressure (bar) | 25 |
| Solvent of BDs fed | water |
| 1,2-BD in BD solution (w %) | 19.0 |
| 1,4-BD in BD solution (w %) | 9.7 |
| $H_2$/BD ratio (molar ratio) | 21.5 |
| WHSV ($h^{-1}$) ($\alpha$) | 0.5 |
| Catalytic performances | | |
| T.O.S. (h) ($\gamma$) | 1 | 71 |
| Benzenediols conversion (%) | 84.3 | 66.9 |
| Selectivity to Phenol (%) | 82.3 | 90.7 |

Notes:
see notes in Example 21

Example 26

| Catalyst | |
|---|---|
| Type of catalyst | CuWO$_4$ |
| Preparation catalyst (see) | Example 5 |
| Operative conditions | |
| Reaction temperature (° C.) | 450 |
| Pressure (bar) | 25 |
| Solvent of BDs fed | water |
| 1,2-BD in BD solution (w %) | 19.0 |
| 1,4-BD in BD solution (w %) | 9.7 |
| $H_2$/BD ratio (molar ratio) | 11.0 |
| WHSV ($h^{-1}$) ($\alpha$) | 0.5 |
| Catalytic performances | |
| T.O.S. (h) ($\gamma$) | 1 |
| Benzenediols conversion (%) ($\delta$) | 87.3 |
| Selectivity to Phenol (%) ($\epsilon$) | 91.2 |

Notes:
see notes in Example 21

Example 27

| Catalyst | |
|---|---|
| Type of catalyst | $Cu_{0.75}Zn_{0.25}WO_4$ |
| Preparation catalyst (see) | Example 7 |
| Operative conditions | |
| Operative conditions as in Example 25 | |
| Catalytic performances | |
| T.O.S. (h) ($\gamma$) | 1 | 25 |
| Benzenediols conversion (%) ($\delta$) | 84.9 | 62.1 |
| Selectivity to Phenol (%) ($\epsilon$) | 79.2 | 87.0 |

Notes:
see notes in Example 21

Example 28

| Catalyst | |
|---|---|
| Type of catalyst | $Cu_{0.75}Zn_{0.25}WO_4$ |
| Preparation catalyst (see) | Example 7 |
| Operative conditions | |
| Operative conditions as in Example 26 | |
| Catalytic performances | |
| T.O.S. (h) ($\gamma$) | 1 |
| Benzenediols conversion (%) ($\delta$) | 89.6 |
| Selectivity to Phenol (%) ($\epsilon$) | 86.1 |

Notes:
see notes in Example 21

Example 29

| Catalyst | |
|---|---|
| Type of catalyst | $CuWO_4 + Ce$ |
| Preparation catalyst (see) | Example 6 |
| Operative conditions | |
| Reaction temperature (° C.) | 450 |
| Pressure (bar) | 25 |
| Solvent of BDs fed | water |
| 1,2-BD in BD solution (w %) | 19.7 |
| 1,4-BD in BD solution (w %) | 10.0 |
| H$_2$/BD ratio (molar ratio) | 21.0 |
| WHSV (h$^{-1}$) ($\alpha$) | 0.5 |
| Catalytic performances | |
| T.O.S. (h) ($\gamma$) | 1 | 45 |
| Benzenediols conversion (%) ($\delta$) | 98.5 | 96.3 |
| Selectivity to Phenol (%) ($\epsilon$) | 85.1 | 81.5 |

Notes:
see notes in Example 21

Example 30

| Catalyst | |
|---|---|
| Type of catalyst | $CuWO_4 + Ce$ |
| Preparation catalyst (see) | Example 6 |
| Operative conditions | |
| Operative conditions as in Example 25 | |
| Catalytic performances | |
| T.O.S. (h) ($\gamma$) | 1 | 24 |
| Benzenediols conversion (%) ($\delta$) | 96.8 | 97.5 |
| Selectivity to Phenol (%) ($\epsilon$) | 91.3 | 92.6 |

Notes:
see notes in Example 21

Example 31

Comparative

| Catalyst | |
|---|---|
| Type of catalyst | VPO |
| Preparation catalyst (see) | Example 8 |
| Operative conditions | |
| Operative conditions as in Example 21 | |
| Catalytic performances | |
| T.O.S. (h) ($\gamma$) | 1 | 21 |
| Benzenediols conversion (%) ($\delta$) | 1.3 | 1.5 |
| Selectivity to Phenol (%) ($\epsilon$) | 58.9 | 73.4 |

Notes:
see notes in Example 21

This example shows that a typical oxidation catalyst, under the operating conditions used for the process, has much lower performances than those obtained with the catalysts object of the present invention.

Example 32

Comparative

| Catalyst | |
|---|---|
| Type of catalyst | $CuO—Al_2O_3$ |
| Preparation catalyst (see) | Example 9 |
| Operative conditions | |
| Reaction temperature (° C.) | 350 |
| Pressure (bar) | 25 |
| Solvent of BDs fed | water |
| 1,2-BD in BD solution (w %) | 18.6 |
| 1,4-BD in BD solution (w %) | 9.4 |
| H$_2$/BD ratio (molar ratio) | 22.2 |
| WHSV (h$^{-1}$) ($\alpha$) | 0.5 |
| Catalytic performances | |
| T.O.S. (h) ($\gamma$) | 25 | 144 |
| Benzenediols conversion (%) ($\delta$) | 99.9 | 82.5 |
| Selectivity to Phenol (%) ($\epsilon$) | 48.8 | 46.1 |

Notes:
see notes in Example 21

This example shows that a typical hydrogenation catalyst, under the operating conditions used for the process, has much lower performances than those obtained with the catalysts object of the present invention.

The invention claimed is:

1. A process for the preparation of phenol by the selective hydroxylation of benzene in the presence of a catalyst based on multi-component metal oxides comprising at least one metal selected from the groups VB, VIB, VIII, IB, IIB, IVA, VA wherein the process comprises:
   feeding oxygen or one or more other oxidizing agents in a lower or zero amount with respect to the stoichiometric quantity of the phenol formed by selectively hydroxylating the benzene with the oxygen or the other oxidizing agents,
   wherein the complementary stoichiometric oxygen is provided by the catalyst, and
   wherein the catalyst contains active oxide phases essentially in crystalline form.

2. A process according to claim 1, further comprising:
restoring, after the selective hydroxylation, the catalyst to an original state with oxygen or another oxidizing compound.

3. A process according to claim 2, in which the selectively hydroxylating and the restoring are effected cyclically.

4. The process according to claim 1, wherein the selective hydroxylation of benzene is carried out in a reactor operating at temperatures of from 150 to 700° C. at a pressure of from 0.1 bar to 100 bar, and with a space velocity (WHSV), calculated with respect to the whole amount of material fed to the reactor, of from 0.01 to 1000 $h^{-1}$.

5. The process according to claim 4, wherein the selective hydroxylation of benzene is carried out at a temperature of from 200 to 600° C.

6. The process according to claim 5, wherein the selective hydroxylation of benzene is carried out at temperatures of from 250 to 550° C.

7. The process according to claim 4, wherein the selective hydroxylation of benzene is carried out at a pressure of from 1 to 30 bar.

8. The process according to claim 4, wherein the selective hydroxylation of benzene is carried out with space velocities of from 1-100 $h^{-1}$.

9. The process according to claim 8, wherein the selective hydroxylation of benzene is carried out with space velocities of from 2 to 50 $h^{-1}$.

10. The process according to claim 1, wherein the selective hydroxylation of benzene is carried out in several reactors of which at least one is devoted to the regeneration of the catalyst, operating either by a physical transfer of the catalyst from a reaction reactor to a regeneration reactor, or by an exchange of flows between the reaction reactor and the regeneration reactor.

11. The process according to claim 1, wherein the selective hydroxylation of benzene is carried out in one or more fluid bed reactors.

12. The process according to claim 1, wherein the selective hydroxylation is carried out in the presence of a catalyst based on multi-component metal oxides comprising at least one metal selected from the group consisting of copper, vanadium, bismuth, molybdenum, niobium, iron, tungsten, zinc, nickel and combinations thereof, optionally containing at least one of antimony and phosphorous.

13. The process according to claim 12, wherein the catalyst is present in a carrier or as a mixture with one or more binders.

14. The process according to claim 1, wherein said oxides comprise at least one active oxide phase which is correlated to the scheelite structure and materials with a non-scheelite crystalline structure or amorphous structure, wherein the scheelite crystalline structure is at least one of the following compositions:

$$Bi_{(1-x/3)}V_{(1-x)}Nb_{(1-x)(1-w)}Mo_xO_4, \text{ and}$$

$$Cu^{(1-z)}Zn_zW_{(1-y)}Mo_yO_4.$$

15. The process according to claim 14, wherein oxides comprise a material with a non-scheelite crystalline or amorphous structure and is capable of increasing the oxygen storage capacity of the structure.

16. The process according to claim 14, wherein the oxides include one or more lanthanide oxides or a mixture thereof with another oxide.

17. The process according to claim 16, wherein the oxides comprise at least one of a cerium oxide and a cerium oxide-zirconium oxide mixture.

18. A process for the preparation of phenol, comprising
selectively hydroxylating benzene in the presence of a catalyst comprising one or more multi-component metal oxides comprising at least one metal selected from the group consisting of a Group VB metal, a Group VIB metal, a Group VIII metal, a Group IB metal, a Group IIB metal, a Group IVA metal, and a Group VA metal;
wherein the selective hydroxylation is carried out by feeding at least one of oxygen and another oxidizing agent to the benzene to the selective hydroxylation in an amount less than the stoichiometric amount required to form the phenol;
wherein the stoichiometric deficiency of the oxygen or the other oxidizing agent fed to the selective hydroxylation is compensated by the catalyst; and
wherein the catalyst contains one or more active oxide phases essentially in crystalline form.

* * * * *